(12) United States Patent
Failli et al.

(10) Patent No.: US 6,297,234 B1
(45) Date of Patent: Oct. 2, 2001

(54) ARYLTHIOPHENE VASOPRESSIN AGONISTS

(75) Inventors: Amedeo A. Failli, Princeton Junction, NJ (US); David K. Williams, Langhorne; Thomas J. Caggiano, Morrisville, both of PA (US); Jay S. Shumsky, Hightstown; Mark A. Ashwell, Plainsboro, both of NJ (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/495,505

(22) Filed: Feb. 1, 2000

Related U.S. Application Data
(60) Provisional application No. 60/155,235, filed on Feb. 4, 1999.

(51) Int. Cl.[7] .................. C07D 409/10; A61K 31/5517; A61P 7/12

(52) U.S. Cl. ............................. 514/220; 540/561

(58) Field of Search .................. 540/561; 514/220

(56) References Cited

U.S. PATENT DOCUMENTS

| | | | |
|---|---|---|---|
| 4,766,108 | 8/1988 | Ali .................................. | 514/16 |
| 5,055,448 | 10/1991 | Manning et al. .................. | 514/16 |
| 5,070,187 | 12/1991 | Gavras et al. .................... | 530/315 |
| 5,512,563 | * 4/1996 | Albright et al. ................. | 514/217 |
| 5,516,774 | 5/1996 | Albright et al. ................. | 514/220 |
| 5,521,173 | * 5/1996 | Venkatesan et al. . | |
| 5,532,235 | 7/1996 | Albright et al. ................. | 514/215 |
| 5,536,718 | 7/1996 | Albright et al. ................. | 514/220 |
| 5,610,156 | 3/1997 | Albright et al. ................. | 514/220 |
| 5,612,334 | 3/1997 | Albright et al. ................. | 514/220 |
| 5,624,923 | 4/1997 | Albright et al. ................. | 514/220 |
| 5,654,297 | 8/1997 | Albright et al. ................. | 514/215 |
| 5,686,445 | 11/1997 | Albright et al. ................. | 514/211 |
| 5,693,635 | 12/1997 | Albright et al. ................. | 514/215 |
| 5,696,112 | 12/1997 | Albright et al. ................. | 514/215 |
| 5,700,796 | 12/1997 | Albright et al. ................. | 514/220 |
| 5,719,278 | 2/1998 | Albright et al. ................. | 540/578 |
| 5,733,905 | 3/1998 | Albright et al. ................. | 514/220 |
| 5,736,538 | 4/1998 | Albright et al. ................. | 514/215 |
| 5,736,540 | 4/1998 | Albright et al. ................. | 514/220 |
| 5,739,128 | 4/1998 | Albright et al. ................. | 514/215 |
| 5,747,487 | 5/1998 | Albright et al. ................. | 514/215 |
| 5,753,648 | 5/1998 | Albright et al. ................. | 514/220 |
| 5,760,031 | 6/1998 | Albright et al. ................. | 514/215 |
| 5,780,471 | 7/1998 | Venkatesan et al. ............. | 514/250 |
| 5,849,735 | 12/1998 | Albright et al. . | |

FOREIGN PATENT DOCUMENTS
| | | |
|---|---|---|
| 08081460 | 3/1996 | (JP) . |
| 9622282 | 7/1996 | (WO) . |

OTHER PUBLICATIONS

Ogawa, HidenoriHiroshi; Kondo, Kazumi; Yamamura, Yoshitaka; Miyamoto, Hisashi; Kan, K.; Kitano, Kazuyoshi; Tanaka, Michinori; Nakaya, K.; et al, J. Med. Chem., 39(18), 3547–3555 (English) 1996.*

(List continued on next page.)

*Primary Examiner*—Mukund J. Shah
*Assistant Examiner*—Thomas C. McKenzie
(74) *Attorney, Agent, or Firm*—Steven R. Eck

(57) ABSTRACT

The present invention provides compounds of the general formula:

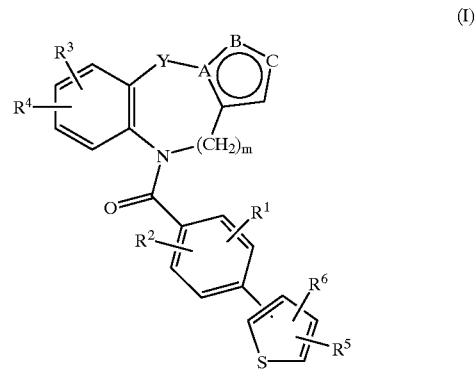

(I)

wherein Y is a moiety selected independently, from NH or —(CH$_2$)$_n$— wherein n is 1; m is an integer from 1 to 2; and the moiety

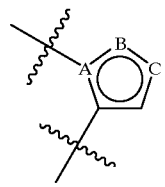

represents: (1) a 5-membered aromatic (unsaturated) heterocyclic ring having one nitrogen (wherein A is nitrogen, and B and C are CH), (2) a 6-membered aromatic (unsaturated) heterocyclic ring having one nitrogen (wherein A is carbon, B is nitrogen, and C is —CH—CH—), (3) a 6-membered aromatic (unsaturated) ring (wherein A is carbon, B is CH, and C is —CH—CH—); as well as methods and pharmaceutical compositions utilizing these compounds for the treatment of disorder which may be remedied or alleviated by vasopressin agonist activity, including diabetes insipidus, nocturnal enuresis, nocturia, urinary incontinence, bleeding and coagulation disorders, or temporary delay of urination.

11 Claims, No Drawings

OTHER PUBLICATIONS

Albright, J. Donald; Reich, Marvin F.; Delos Santos, Efren G.; Dusza, John P.; Sum, Fuk–Wah; Venkatesan, Aranapakam M.; Coupet, Joseph; Chan, Peter S.; Ru, Xun; Mazandarani, Hossein; Bailey, Trina, J. Med. Chem., 41(14), 2442–2444 (English) 1998.*
Ruffolo et al, Drug News and Perspectives, 4, 1991, 217–222.*
Cervoni and Chan, Encylc. Of Chem. Tech., $4^{th}$ ed., 8, 398–432 (1993).
Oliver et al., J. Physiol. (London), 18, 277–279 (1895).
du Vigneaud et al., J. Am. Chem. Soc., 76, 4751–4752 (1954).
Jackson, Pharm. Basis of Ther., $9^{th}$ ed., 715–731 (1996).
Lethagen, Ann. Hematol., 69, 173–180 (1994).
Cash et al., Brit. J. Haematol, 27, 363–364 (1974).
David, Regulatory Peptides, 45, 311–317 (1993).
Burggraaf et al., Cli. Sci., 86, 497–503 (1994).
Manning et al., J. Med. Chem., 35, 382 (1992).
Manning et al., J. Med. Chem., 35, 3895 (1992).
Ruffolo et al., Drug News and Perspectives, 4(4), 217 (May 1991).
Albright et al., Curr. Pharm. Des., 3(6), 615 (1997).
Williams et al., J. Med. Chem., 35, 3905 (1992).
Huguenin et al., Helv. Chem. Acta, 49, 695 (1966).
Huguenin et al., Helv. Chem. Acta, 49, 695 (1966) (translation).

* cited by examiner

ARYLTHIOPHENE VASOPRESSIN AGONISTS

This application claims the benefit of U.S. Provisional Application No. 60/155,235, which was converted from U.S. patent application Ser. No. 09/244,179, filed Feb. 4, 1999, pursuant to a petition filed under 37 C.F.R. 1.53(c)(2)(i).

This invention concerns tricyclic arylthiophene compunds which act as vasopressin $V_2$ agonists, as well as methods of treatment and pharmaceutical compositions utilizing these compounds.

BACKGROUND OF THE INVENTION

Vasopressin (antidiuretic hormone, ADH) a nonapeptide hormone and neurotransmitter, is synthesized in the supraoptic nuclei of the hypothalamus of the brain and transported through the supraoptico-hypophyseal tract to the posterior pituitary where it is stored. Upon sensing an increase in plasma osmolality by brain osmoreceptors or a decrease in blood volume or blood pressure (detected by the baroreceptors and volume receptors), vasopressin is released into the blood circulation and activates vasopressin $V_{1a}$ receptors on blood vessels causing vasoconstriction to raise blood pressure; and vasopressin $V_2$ receptors of the nephron of the kidney causing reabsorption mainly of water and to a lesser degree electrolytes, to expand the blood volume (Cervoni and Chan, *Diuretic Agents,* in Kirk-Othmer, Encyclopedia of Chemical Technology, 4th ed., Wiley, Volume 8, 398–432, (1993)). The existence of vasopressin in the pituitary was known as early as 1895 (Oliver and Schaefer, *J. Physiol.* (London), 18, 277–279, (1895)). The determination of the structure and the total synthesis of vasopressin were accomplished by du Vigneaud and coworkers in 1954 (du Vigneaud, Gish and Katsoyannis, *J. Am. Chem. Soc.,* 76, 4751–4752, (1954)).

The actions of vasopressin $V_{1a}$ receptors are mediated through the phosphatidylinositol pathway. Activation of vasopressin $V_{1a}$ receptors causes contraction of the smooth muscle of the blood vessels to raise blood pressure. The actions of the vasopressin $V_2$ receptors are mediated through activation of the adenylate cyclase system and elevation of intracellular levels of cAMP. The activation of vasopressin $V_2$ receptors by vasopressin or vasopressin-like (peptidic or non-peptidic) compounds increases water permeability of the collecting ducts of the nephron and permits the reabsorption of a large quantity of free water. The end result is the formation and excretion of a concentrated urine, with a decrease in urine volume and an increase in urinary osmolality.

Vasopressin plays a vital role in the conservation of water by concentrating the urine at the site of the collecting ducts of the kidney. The collecting ducts of the kidney are relatively impermeable to water without the presence of vasopressin at the receptors and therefore, the hypotonic fluid formed after filtering through the glomeruli, passing the proximal convoluted tubule, the loops of Henle, and the distal convoluted tubules, will be excreted as dilute urine. However, during dehydration, volume depletion or blood loss, vasopressin is released from the brain and activates the vasopressin $V_2$ receptors in the collecting ducts of the kidney rendering the ducts very permeable to water; hence water is reabsorbed and a concentrated urine is excreted. In patients and animals with central or neurogenic diabetes insipidus, the synthesis of vasopressin in the brain is defective and therefore, they produce very little or no vasopressin, but their vasopressin receptors in the kidneys are normal. Because they cannot concentrate the urine, they may produce as much as 10 times the urine volumes of their healthy counterparts and they are very sensitive to the action of vasopressin and vasopressin $V_2$ agonists. Vasopressin and desmopressin, which is a peptide analog of the natural vasopressin, are being used in patients with central diabetes insipidus. Vasopressin $V_2$ agonists are also useful for the treatment of nocturnal enuresis, nocturia, urinary incontinence and temporary delay of urination whenever desirable.

Vasopressin, through activation of its $V_{1a}$ receptors, exerts vasoconstricting effects so as to raise blood pressure. A vasopressin $V_{1a}$ receptor antagonist will counteract this effect. Vasopressin and vasopressin-like agonists release factor VIII and von Willebrand factor so they are useful for the treatment of bleeding disorders, such as hemophilia. Vasopressin and vasopressin-like agonists also release tissue-type plasminogen activator (t-PA) into the blood circulation so they are useful in dissolving blood clots such as in patients with myocardial infarction and other thromboembolic disorders (Jackson, "Vasopressin and other agents affecting the renal conservation of water", in Goodman and Gilman, *The Pharmacological Basis of Therapeutics,* 9th ed., Hadman, Limbird, Molinoff, Ruddon and Gilman Eds., McGraw-Hill, New York, pp. 715–731 (1996); Lethagen, *Ann. Hematol.* 69, 173–180 (1994); Cash et al., *Brit. J. Haematol.,* 27, 363–364 (1974); David, *Regulatory Peptides,* 45, 311–317 (1993); Burggraaf et al., *Cli. Sci.,* 86, 497–503 (1994)).

The following prior art references describe peptidic vasopressin antagonists: Manning et al., *J. Med. Chem.,* 35, 382 (1992); Manning et al., *J. Med. Chem.,* 35, 3895 (1992); Gavras and Lammek, U.S. Pat. No. 5,070,187 (1991); Manning and Sawyer, U.S. Pat. No. 5,055,448 (1991); Ali, U.S. Pat. No. 4,766,108 (1988); Ruffolo et al., *Drug News and Perspectives* 4(4), 217 (May 1991); Albright and Chan, *Curr. Pharm. Des.* 3(6), 615 (1997). Williams et al., have reported on potent hexapeptide oxytocin antagonists [*J. Med Chem.,* 35, 3905 (1992)] which also exhibit weak vasopressin antagonistic activity in binding to $V_1$ and $V_2$ receptors. Peptidic vasopressin antagonists suffer from a lack of oral activity and many of these peptides are non-selective antagonists since they also exhibit partial agonist activity.

Non-peptidic vasopressin antagonists have recently been disclosed. Albright et al. describe tricyclic azepines as vasopressin antagonists or vasopressin and oxytocin antagonists in U.S. Pat. No. 5,516,774 (1996), U.S. Pat. No, 5,532,235 (1996), U.S. Pat. No. 5,536,718, U.S. Pat. No. 5,610,156 (1997), U.S. Pat. No. 5,612,334 (1997), U.S. Pat. No. 5,624,923 (1997), U.S. Pat. No. 5,654,297 (1997), U.S. Pat. No. 5,686,445 (1997), U.S. Pat. No. 5,693,635 (1997), U.S. Pat. No. 5,696,112, U.S. Pat. No. 5,700,796 (1997), U.S. Pat. No. 5,719,278 (1998), U.S. Pat. No. 5,733,905 (1998), U.S. Pat. No. 5,736,538 (1998), U.S. Pat. No. 5,736,540 (1998), U.S. Pat. No. 5,739,128 (1998), U.S. Pat. No. 5,747,487 (1998), U.S. Pat. No. 5,753,648 (1998), U.S.

Pat. No. 5,760,031 (1998), U.S. Pat. No. 5,780,471 (1998); tetrahydrobenzodiazepine derivatives as vasopressin antagonists are disclosed in J.P. 0801460-A (1996); Ogawa et al., disclose benzoheterocyclic derivatives as vasopressin and oxytocin antagonists, and as vasopressin agonists in WO 9534540-A; and Venkatesan et al., disclose tricyclic benzazepine derivatives as vasopressin and oxytocin antagonists in U.S. Pat. No. 5,521,173 (1996).

As mentioned above, desmopressin (1-desamino-8-D-arginine vasopressin) (Huguenin and Boissonnas, *Helv. Chim. Acta*, 49, 695 (1966)) is a vasopressin agonist. The compound is a synthetic peptide with variable bioavailability. An intranasal route is poorly tolerated and an oral formulation for nocturnal enuresis requires a 10–20 fold greater dose than the intranasal administration.

Albright et al. disclose (cf. examples 1 and 6), a subset of tricyclic pyrrolo benzodiazepines which are part of the present application, as $V_1$ and/or $V_2$ vasopressin receptor antagonists and oxytocin receptor antagonists in U.S. Pat. No. 5,521,173 (1996), inter alia.

Compounds of general structure 7a in Scheme I U.S. Pat. No. 5,521,173 are taught by Albright et al. to possess antagonist activity at $V_1$ and/or $V_2$ receptors and exhibit in vivo vasopressin antagonist activity, as well as antagonist activity at oxytocin receptors.

Scheme I

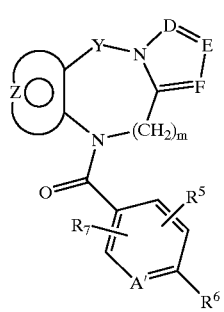

7a (Albright et al.) U.S. Pat. No. 5,521,173 wherein m is 1; Y is a moiety selected from $(CH_2)_n$ wherein n is 1; D, E, and F are selected from carbon; $A^1$ is CH; $R^6$ is the moiety:

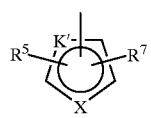

$K^1$ is CH; X is S; $R^5$ is hydrogen; $R^7$ is hydrogen; and the moiety:

represents a fused phenyl or optionally substituted phenyl.

Also, Albright et al. broadly disclose a subset of tricyclic pyrrolo and pyrido benzodiazepines, part of the present application, as $V_1$ and/or $V_2$ vasopressin receptor antagonists and oxytocin receptor antagonists in WO 96/22282 A1 (1996), inter alia.

Compounds of general structure 61b in Scheme 12 of the above application, are claimed by Albright et al. to possess antagonist activity at $V_1$ and/or $V_2$ receptors and exhibit in vivo vasopressin antagonist activity, as well as antagonist activity at oxytocin receptors.

Scheme 12

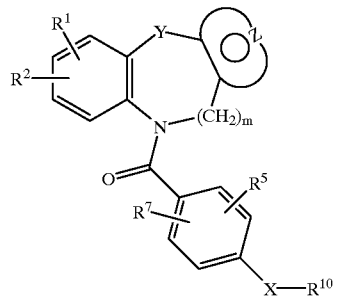

61b (Albright et al.) WO 96/22282 A1 wherein m is 1; Y is a NH or a moiety selected from $(CH_2)_n$ wherein n is 1; $R^5$ and $R^7$ are selected from hydrogen; X is direct bond; $R^{10}$ represents the moiety

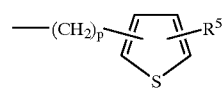

p is 0; $R^1$ and $R^2$ are selected from hydrogen, $(C_1-C_3)$ lower alkyl, $(C_1-C_3)$ lower alkoxy and halogen; and the moiety

represents an optionally substituted phenyl, a 5-membered aromatic (unsaturated) heterocyclic ring having one nitrogen atom, or a 6-membered aromatic (unsaturated) heterocyclic ring having one nitrogen atom.

However, certain tricyclic pylrrolo- and pyridobenzodiazepines of general structure 7b and 61b have been found unexpectedly to be vasopressin $V_2$ receptor agonists in vivo, and thus possess different biological profile and clinical utility from those originally disclosed. Thus, rather than having an aquaretic effect they do unexpectedly cause reabsorption of water, i.e they reduce urine volume and increase urine osmolality.

The compounds of this invention are non-peptidic and have a good oral bioavailability. They are vasopressin $V_2$ receptor agonists, and as such they promote reabsorption of water. They have no vasopressin $V_{1a}$ receptor agonist effects so they do not raise blood pressure. In contrast, the prior art compounds are described as vasopressin antagonists at both the $V_{1a}$ and $V_2$ receptors.

SUMMARY OF THE INVENTION

This invention relates to novel and known compounds selected from those of formula (I):

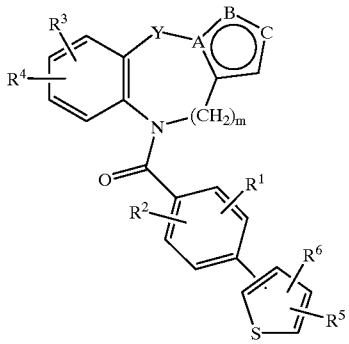

(I)

wherein:
   Y is a moiety selected independently, from NH or —(CH$_2$)$_n$— wherein n is 1; m is an integer from 1 to 2;
   R$^1$, R$^2$, R$^5$ and R$^6$ are independently, selected from hydrogen, lower alkyl (C$_1$–C$_6$), lower alkoxy (C$_1$–C$_6$), halogen, and CF$_3$;
   R$_3$ and R$_4$ are independently, selected from the group comprising hydrogen, lower alkyl (C$_1$–C$_6$), halogen, amino, (C$_1$–C$_6$) lower alkoxy, or (C$_1$–C$_6$) lower alkylamino;
   and the moiety

represents:
   (1) a 5-membered aromatic (unsaturated) heterocyclic ring having one nitrogen (wherein A is nitrogen, and B and C are CH);
   (2) a 6-membered aromatic (unsaturated) heterocyclic ring having one nitrogen (wherein A is carbon, B is nitrogen, and C is CH—CH);
   (3) a 6-membered aromatic (unsaturated) ring (wherein A is carbon, B is CH, and C is —CH—CH—);
or a pharmaceutically acceptable salt, or pro-drug form thereof.

Preferred compounds of this invention include:

(4-Thiophen-2-yl-phenyl)-(5H-10,11-dihydro-pyrrolo [2,1-c][1,4] benzodiazepin-10-yl)-methanone;

[4-(5-Bromo-thiophen-2-yl)-phenyl]-(5H-10,11-dihydro-pyrrolo [2,1c][1,4] benzodiazepin-10-yl)-methanone;

[2-Chloro-4-(5-chloro-thiophen-3-yl)-phenyl]-(5H- 10,11-dihydro-pyrrolo [2,1-c][1,4] benzodiazepin-10-yl)-methanone;

(2-Chloro-4thiophen-2-yl-phenyl)-(5H-10,11-dihydro-pyrrolo [2,1-c][1,4] benzodiazepin-10-yl)-methanone;

[2-Chloro-4-(5-chloro-thiophen-2-yl)-phenyl]-(5H-10,11-dihydro-pyrrolo [2,1-c][1,4] benzodiazepin-10-yl)-methanone;

[2-Chloro-4-(5-methyl-thiophen-2-yl)-phenyl]-(5H-10,11-dihydro-pyrrolo [2,1-c][1,4] benzodiazepin-10-yl)-methanone;

(2-Chloro-4-thiophen-3-yl-phenyl)-(5H-10,11-dihydro-pyrrolo [2,1-c][1,4] benzodiazepin-10-yl)-methanone;

[2-Chloro-4-(5-chloro-thiophen-3-yl)-phenyl]-(5H-10,11-dihydro-pyrrolo [2,1-c][1,4] benzodiazepin- 10-yl)-methanone;

(2-Methyl-4-thiophen-2-yl-pbenyl)-(5,11-dihydro-pyrido [2,3-b][1,5] benzodiazepin-10-yl)-methanone; and

[2-Chloro-4-(5-chloro-thiophen-2-yl)-phenyl]-(5,11-dihydro-pyrido [2,3-b][1,5] benzodiazepin-10-yl)-methanone.

(2-Chloro-4-thiophen-3-yl-phenyl)-(5,11-dihydro-pyrido [2,3-b][1,5] benzodiazepin-10-yl)-methanone.

It is understood by those in the art that some of the compounds of this invention depending on the definition of R$^1$, R$^2$, R$^3$, and R$^4$ may contain one or more asymmetric centers and may thus give rise to optical isomers and diastereomers. The present invention includes such optical isomers and diastereomers; as well as the racemic and resolved, enantiomerically pure R and S stereoisomers and pharmaceutically acceptable salts thereof, which possess the indicated activity. Optical isomers may be obtained in pure form by standard procedures known to those skilled in the art. It is also understood that this invention encompasses all possible regioisomers, and mixtures thereof which possess the indicated activity. Such regioisomers may be obtained in pure form by standard separation procedures known to those skilled in the art.

Also according to the present invention there is provided a method of treating or preventing disorders which are remedied or alleviated by vasopressin receptor agonist. Methods of this invention for inducing vasopressin agonism in a mammal include, but are not limited to, methods of treating, alleviating or preventing diabetes insipidus, nocturnal enuresis, nocturia, urinary incontinence, bleeding and coagulation disorders, and temporary delay of urination whenever desirable in humans or other mammals, which comprises administering to a human or other mammal an effective amount of a compound or a pharmaceutical composition of the invention.

The present invention accordingly provides a pharmaceutical composition which comprises a compound of this invention in combination or association with a pharmaceutically acceptable carrier. In particular, the present invention provides a pharmaceutical composition which comprises an effective amount of a compound of this invention and a pharmaceutically acceptable carrier.

The compositions are preferably adapted for oral administration. However, they may be adapted for other modes of administration, for example, parenteral administration for patients suffering from coagulation disorders.

In order to obtain consistency of administration, it is preferred that a composition of the invention is in the form of a unit dose. Suitable unit dose forms include tablets, capsules and powders in sachets or vials. Such unit dose forms may contain from 0.1 to 1000 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day. The compositions of the invention may be formulated with conventional excipients, such as a filler, a disintegrating agent, a binder, a lubricant, a flavoring agent and the like. They are formulated in conventional manner, for example, in a manner similar to that used for known antihypertensive agents, diuretics and β-blocking agents.

Also according to the present invention there are provided processes for producing the compounds of the present invention.

PROCESS OF THE INVENTION

The compounds of the present invention of general formula (I) may conveniently be prepared according to the process shown in Scheme 1.

*Soc. Jpn.*, 52, 1989 (1979). Treatment of said mixed anhydride of general formula (2) with the tricyclic benzodiazepine of formula (1) in a solvent such as dichloromethane and in the presence of an organic base at temperatures ranging from 0° C. to the reflux temperatures of the solvent, yields the intermediate acylated derivative (3) of Scheme (I).

The acylating intermediate of formula (2) is ultimately chosen on the basis of its compatibility with the $R^1$, $R^2$, $R^3$ and $R^4$ groups, and its reactivity with the tricyclic benzodiazepine of formula (1).

Reaction of a compound of formula (3, X=Br or I) with an appropriately substituted thiophene boronic acid of formula (4, wherein $R^5$ and $R^6$ are hereinbefore defined, and

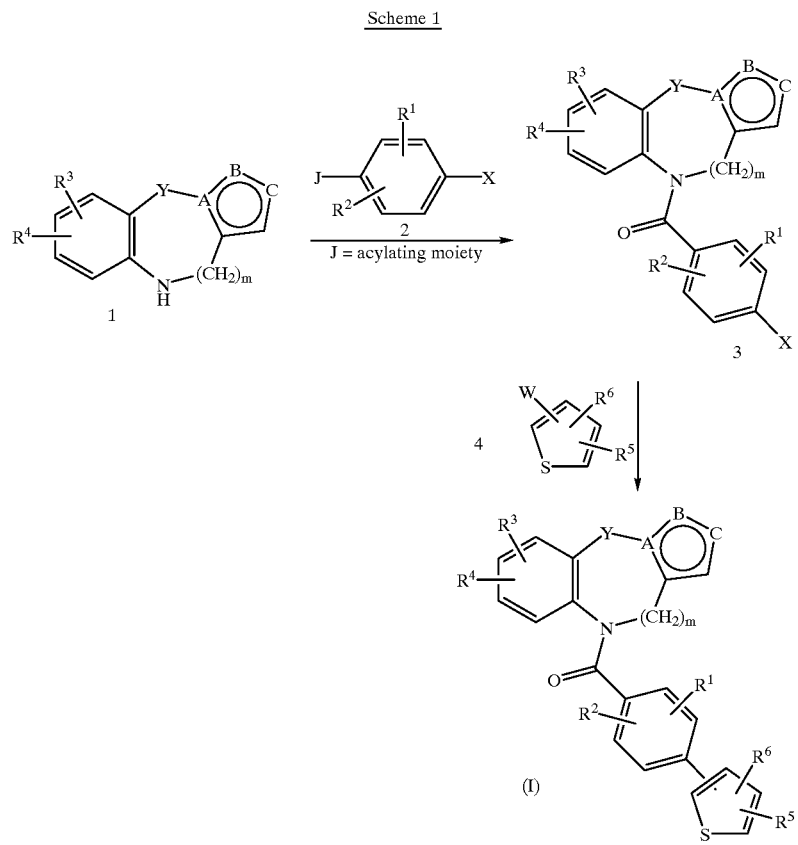

Thus, a tricyclic benzodiazepine of formula (1, wherein m, Y, A, B, C, $R^3$ and $R^4$ are hereinbefore defined) is reacted with an appropriately substituted acylating agent such as a haloaroyl halide, preferably a bromoaroyl (iodoaroyl) chloride of formula (2, wherein J=COCl, X=Br or I, and $R^1$, $R^2$ are hereinbefore defined) in the presence of an inorganic base such as potassium carbonate in a polar, aprotic solvent such as N,N-dimethylformamide; or an organic base in an aprotic solvent such as dichloromethane or tetrahydrofuran at temperatures ranging from −40° C. to 50° C. to yield the intermediate acylated derivative (3).

Alternatively, the acylating species can be a mixed anhydride of the corresponding carboxylic acid, such as that prepared treating said acid with 2,4,6-trichlorobenzoyl chloride in an aprotic organic solvent such as dichloromethane according to the procedure of Inanaga et al., *Bull. Chem.*

W=B(OH)$_2$) in a mixture of solvents such as toluene-ethanol-water, and in the presence of a Pd(0) catalyst and a base such as sodium carbonate at temperatures ranging from ambient to the reflux temperature of the solvent, yields the desired compounds of formula (I, wherein Y, m, A, B, C, $R^1$, $R^2$, $R^3$, $R^4$, $R^5$ and $R^6$ are as defined above).

Alternatively, a compound of formula (3, X=I) is reacted with an appropriately substituted thiophene tri-alkyltin derivative of formula (4, wherein $R^5$, and $R^6$ are hereinbefore defined, and W=Sn(alkyl)$_3$) to afford the desired compound of formula (I, wherein Y, m, A, B, C, $R^1$, $R^2$, $R^3$, $R^4$, $R^5$ and $R^6$ are as defined above).

The preferred substituted 4-bromo(iodo) aroyl chlorides of formula (2) of Scheme I (X=Br or I, J=COCl) are either available commercially, or are known in the art, or can be readily prepared by procedures analogous to those in the literature for the known compounds.

The preferred substituted thiophene boronic acids of formula (4, W=B(OH)₂) are either available commercially, or or are known in the art, or can be readily prepared by procedures analogous to those in the literature for the known compounds.

The preferred substituted thiophene tri-alkylstannanes of formula (4, W=Sn(alkyl)₃) of Scheme I are either available commercially, or can be conveniently prepared as shown in Scheme II. Thus, the corresponding bromo starting materials of formula (5, wherein W=Br, and R⁵ and R⁶ are hereinbefore defined) are first reacted with n-butyl lithium followed by treatment of the intermediate lithiated species with a tri-alkyl (preferably tri-methyl or tri-n-butyl) tin chloride to give the desired thiophene stannane intermediates (4, wherein W=Sn(alkyl)₃), and R⁵ and R⁶ are hereinbefore defined)

Scheme II

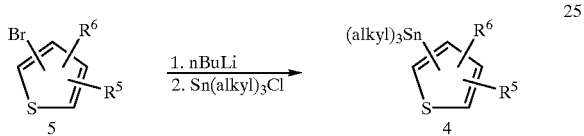

Alternatively, as shown in Scheme III, the bromo derivative (3) of Scheme I (wherein X=Br, and Y, m, A, B, C, R¹, R², R³ and R⁴ are hereinbefore defined) is reacted with an hexa-alkyl-di-tin in the presence of a palladium (0) catalyst and lithium chloride to yield the tri-(alkyl)tin intermediate of formula (6). Further reaction of (6) with the appropriately substituted thiophene halide of formula (5, wherein X=Br or I, and R⁵ and R⁶ are hereinbefore defined) in the presence of a palladium(0) catalyst provides the desired compounds of formula (I) of Scheme I.

Scheme III

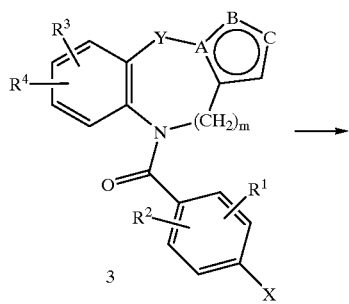

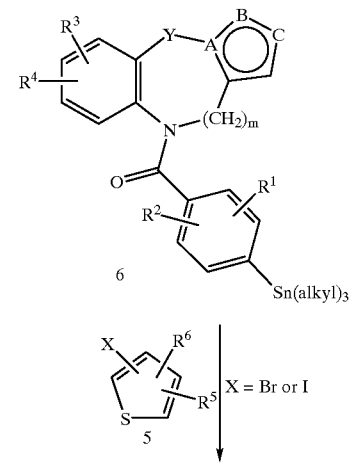

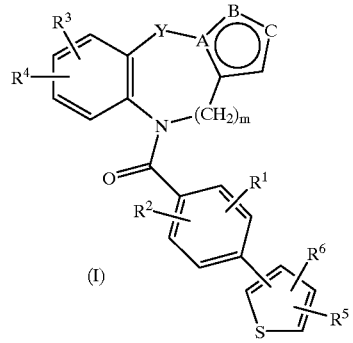

The desired compounds of formula (I) of Scheme I can be alternatively, prepared by the process shown in Scheme IV. Thus, an appropriately substituted carboxylic acid derivative of formula (7, wherein P is a carboxylic acid protecting group, preferably P=alkyl or benzyl), is reacted with a thiophene tri-(alkyl)tin derivative (4) in the presence of a palladium (0) catalyst to provide the intermediate ester (8). Subsequent unmasking of the carboxylic function followed by activation of the intermediate acid (9) using any of the procedures hereinbefore described, and coupling of the intermediate (10) to the tricyclic benzodiazepine of formula (1) provides the desired compounds (I) wherein Y, m, A, B, C, R¹, R², R³, R⁴, R⁵ and R⁶ are as defined above.

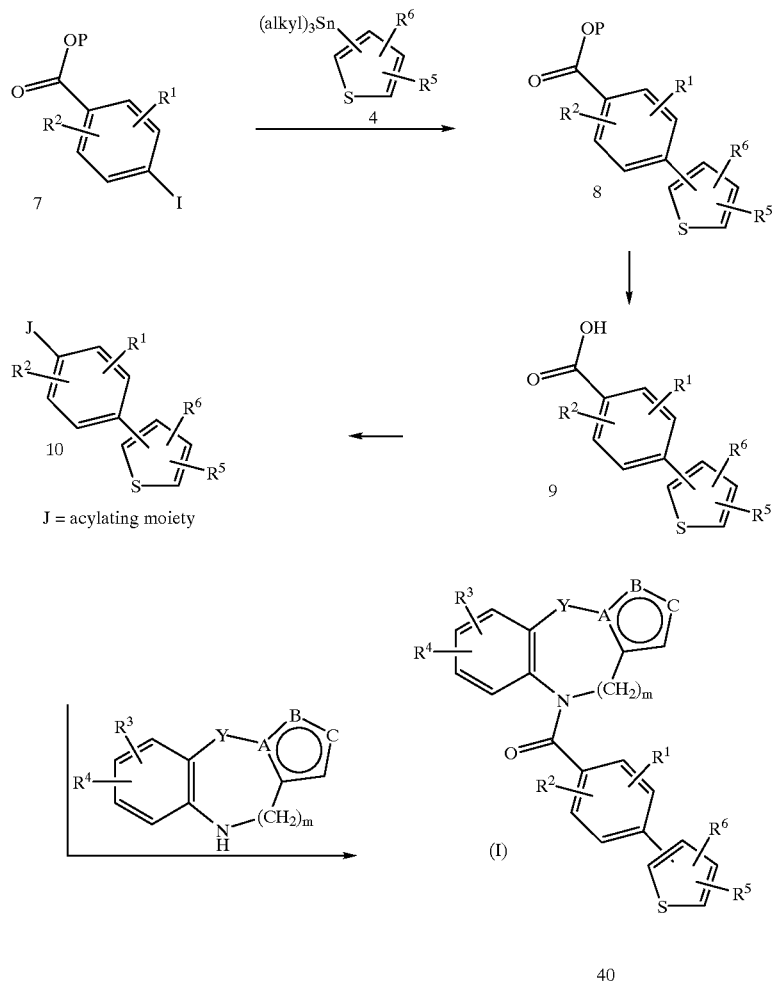

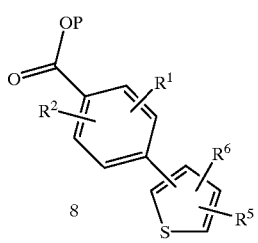

Alternatively, the desired intermediates of formula (8) of Scheme IV can be prepared from (7) and the thiophene boronic acid derivative of formula (4, wherein W=B(OH)$_2$) in a mixture of solvents such as toluene-ethanol-water, in the presence of a palladium(0) catalyst and a base such as sodium carbonate at temperatures ranging from ambient to the reflux temperature of the solvent, as shown in Scheme V.

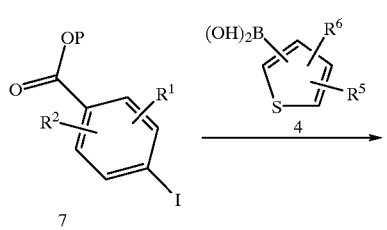

The compounds of formula (I) that are 5-substituted 2-alkylthiophenes can be conveniently prepared as shown in Scheme VI, by reaction of the intermediate bromide of formula (3) with a 2-alkyl thiophene of formula 11 in the presence of a palladium(0) catalyst, potassium acetate and a solvent such as N,N-dimethyacetamide in a Carius tube at temperatures up to 150° C., essentially according to the procedure of Ohta et al., *Heterocycles,* 31, 1951 (1990).

Scheme VI

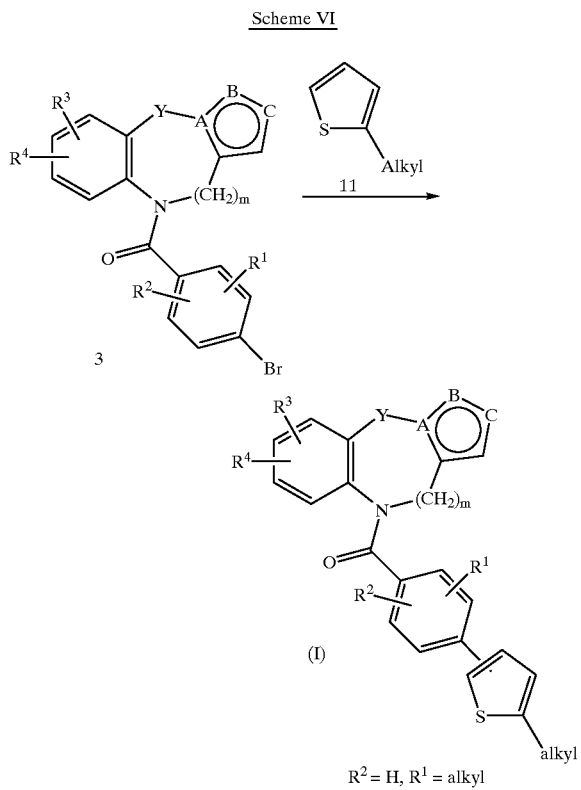

The subject compounds of the present invention were tested for biological activity according to the following procedures.

Vasopressin $V_2$ Agonist Effects of Test Compounds in Normal Conscious Water-Loaded Rats Male or female normotensive Sprague-Dawley rats (Charles River Laboratories, Inc., Kingston, N.Y.) of 350–500 g body weight were supplied with standard rodent diet (Purina Rodent Lab. Chow 5001) and water ad lithium. On the day of test, rats were placed individually into metabolic cages equipped with devices to separate the feces from the urine and containers for collection of urine. A test compound or a reference agent was given at an oral dose of 10 mg/Kg in a volume of 10 mL/Kg. The vehicle used was 20% dimethylsulfoxide (DMSO) in 2.5% preboiled corn starch. Thirty minutes after dosing the test compound, rats were garaged with water at 30 mL/Kg into the stomach using a feeding needle. During the test, rats were not provided with water or food. Urine was collected for four hours after dosing of the test compound. At the end of four hours, urine volume was measured. Urinary osmolality was determined using a Fiske One-Ten Osmometer (Fiske Associates, Norwood, Mass., 02062) or an Advanced CRYOMATIC Osmometer, Model 3C2 (Advanced Instruments, Norwood, Mass.). Determinations of $Na^+$, $K^+$ and $Cl^-$ ion were carried out using ion specific electrodes in a Beckman SYNCHRON EL-ISE Electrolyte System analyzer. The urinary osmolality should increase proportionally. In the screening test, two rats were used for each compound. If the difference in the urine volume of the two rats was greater than 50%, a third rat was used.

The results of this study are shown in Table 1.

TABLE 1

| Example | Urine Volume (% decrease)[a] | Changes in Urinary Osmolality[b] | Rat Type[c] |
|---|---|---|---|
| 1 | 68 | 224 | CD |
| 2 | 74 | 819 | CD |
| 3 | 71 | 190 | CD |
| 4 | 74 | 365 | CD |
| 5 | 63 | 180 | CD |
| 6 | 75 | 286 | CD |
| 7 | 75 | 282 | CD |
| 8 | 44 | 143 | CD |

[a]Percent decrease in urine volume vs control at a dose of 10 mg/Kg
[b]Percent changes in osmolality vs control at a dose of 10 mg/Kg
[c]Rat model used: Sprague-Dawley (CD)

The following examples are presented to illustrate rather than limit the scope of the invention.

EXAMPLE 1

(2-Chloro-4-thiophen-2-yl-phenyl)-(5H-10,11-dihydro-pyrrolo [2,1-c][1,4] benzodiazepin-10-yl)-methanone Step A (4-Bromo-2-chloro-phenyl)-(5H,11H-pyrrolo [2,1-c][1,4]benzodiazepin-10-yl)-methanone N,N-dimethylformamide (1 drop) was added to a solution of 4-bromo-2-chlorobenzoic acid (2.30 g) in anhydrous tetrahydrofuran (20 mL). Oxalyl chloride (1.46 g) was added and the mixture was warmed to reflux. The resultant solution was cooled to ambient temperature before being evaporated to dryness to give crude 4-bromo-2-chlorobenzoyl chloride as a gold, viscous liquid, which was used without further purification.

To a mixture of 10,11-dihydro-5H-pyrrolo [2,1-c][1,4] benzodiazepine (1.44 g) and triethylamine (0.95 g) in dichloromethane (40 mL) cooled in an ice bath, was added dropwise a solution of the crude 4-bromo-2-chlorobenzoyl chloride (2.42 g) in dichloromethane (20 mL). The cooling bath was removed and after stirring for 22 hours, the reaction mixture was sequentially washed with water, saturated aqueous sodium bicarbonate, 0.5 N hydrochloric acid and water. The dichloromethane solution was dried over anhydrous sodium sulfate, filtered and then evaporated to dryness to yield an off-white foam. Purification by flash chromatography on silica gel Merck-60 eluting with hexane-ethyl acetate (2:1) resulted in a white solid (3.02 g), m.p. 77–80° C.

MS (EI, m/z); 400 $[M]^+$

Step B (2-Chloro4-thiophen-2-yl-phenyl)-(5H-10,11-dihydro-pyrrolo [2,1-c][1,4] benzodiazepin-10yl)-methanone Thiophene-2-boronic acid (0.51 g, 4 mmol) was added to a mixture of (4-bromo-2-chloro-phenyl)-(5H,11H-pyrrolo [2,1-c][1,4] benzodiazepin-10-yl)-methanone of Step A (1.61 g, 4 mmol) and sodium carbonate (1.02 g, 9.6 mmol) in toluene (36 mL), ethanol (10 mL) and water (20 mL). The resultant solution was purged with nitrogen for 15 minutes, and then tetrakis (triphenylphosphine) palladium(0) catalyst (0.18 g, 0.16 mmol) was added. The reaction mixture was heated to reflux for 17 hours, cooled to ambient temperature, stirred for an additional 26 hours and filtered through Celite, which was then rinsed with ethyl acetate. The combined filtrate was diluted to 140 mL with water/ethyl acetate (1:1). The ethyl acetate extracts were dried over anhydrous magnesium sulfate, filtered and evaporated to dryness. The residue (brown foam) was flash chromatographed on silica gel Merck-60 (eluant: hexane-ethyl acetate 4:1) to yield an off-white foam, which was redissolved in dichloromethane. Addition of hexane provided the title compound as a white powder, m.p. 129.5–132° C.

$^1$H NMR (DMSO-$d_6$, 400 MHz): δ5.28 (br m, 4H), 5.90 (t, 1H), 5.99 (s, 1H), 6.82 (s, 1H), 7.10 (m, 4H), 7.40 (m, 3H), 7.60 (d, 2H), 7.64 (s, 1H)

MS (EI, m/z): 404 [M]$^+$

Anal. Calcd. for $C_{23}H_{17}ClN_2OS$: C, 68.22; H, 4.23; N, 6.92. Found: C, 68.30; H, 4.26; N, 6.74

EXAMPLE 2

[2-Chloro4-(5-chloro-thiphen-2-yl)-phenyl]-(5H-10,11-dihydropyrrolo [2,1-c][1,4] benzodiazepin-10-yl)-methanone 5-Chloro-thiophene-2-boronic acid (0.65 g, 4 mmol) was added to a mixture of (4-bromo-2-chloro-phenyl)-(5H, 11H-pyrrolo [2,1-c][1,4] benzodiazepin-10-yl)-methanone of Example 1, Step A (1.61 g, 4 mmol) and sodium carbonate (1.02 g, 0.6 mmol) in toluene (36 mL), ethanol (10 mL) and water (20 mL). The resulting solution was purged with nitrogen for 10 minutes, and then tetrakis (triphenylphosphine) palladium(0) catalyst (0.18 g, 0.16 mmol) was added. The solution was heated at reflux for 41 hours, cooled to ambient temperature and filtered through Celite, which was rinsed with ethyl acetate. The combined filtrate was diluted to 140 mL with water/ethyl acetate (1:1), and the combined organic extracts were dried over anhydrous magnesium sulfate, filtered and evaporated to dryness. The residue (brown foam) was flash chromatographed on silica gel Merck-60 (eluant: hexane-ethyl acetate 4:1) to yield a white foam which was redissolved in dichloromethane. Addition of hexane provided the title compound as an off-white solid, m.p. 119.5–122° C.

$^1$H NMR (DMSO-$d_6$, 400 MHz): δ5.28 (br m, 4H), 5.90 (t, 1H), 5.99 (s, 1H), 6.81 (s, 1H), 7.10 (m, 4H), 7.40 (d, 3H), 7.50 (d, 1H), 7.64 (s, 1H)

MS (+FAB, m/z): 461 [M+Na]$^+$, 439 [M+H]$^+$

Anal. Calcd. for $C_{23}H_{16}Cl_2N_2OS$: C, 62.88; H, 3.67; N, 6.38. Found: C, 62.52; H, 3.69; N, 6.27

EXAMPLE 3

[2-Chloro-4-(5-methyl-thiophen-2-yl)-phenyl]-(5H-10,11-dihydro-pyrrolo [2,1-c][1,4] benzodiaze in-10-yl)-methanone The title compound was prepared essentially according to the conditions set forth by Ohta et al., *Heterocycles*, 31, 1951 (1990). Potassium acetate (0.44 g, 4.5 mmol) was added to a solution of (4-bromo-2-chloro-phenyl)-(5H,11H-pyrrolo [2,1-c][1,4] benzodiazepin-10-yl)-methanone of Example 1, Step A (1.2 g, 3 mmol) and 2-methylthiophene (1.5 mL, 15.49 mmol) in N,N-dimethyl acetamide (7.5 mL), in a 15 mL Carius tube. The resultant solution was purged with nitrogen for 15 minutes, then tetrakis (triphenylphosphine) palladium(0) catalyst (0.17 g, 0.15 mmol) was added. The sealed tube was heated in an oil bath at 150° C. for 16.5 hours. The solvent was removed in vacuo, and the residue was triturated with water (10 mL) and extracted with dichloromethane. The organic extracts were dried over anhydrous sodium sulfate, filtered and evaporated to yield a dark brown oil. Flash chromatography of the residue on silica gel Merck-60 (eluant: hexane-ethyl acetate 2:1) resulted in an off-white foam which was redissolved in dichloromethane. Addition of hexane provided the title compound as an off-white powder, m.p. 154–155.5° C.

$^1$H NMR (DMSO-$d_6$, 400 MHz): δ2.43 (s, 3H) 5.27 (br m, 4H), 5.90 (t, 1H), 5.98 (s, 1H), 6.81 (m, 2H), 7.04 (m, 3H), 7.32 (s, 2H), 7.39 (d, 2H), 7.55 (s, 1H)

MS (EI, m/z): 418[M]$^+$

Anal. Calcd. for $C_{24}H_{19}ClN_2OS$: C, 68.81; H, 4.57; N, 6.69. Found: C, 68.77; H, 4.69; N, 6.61

EXAMPLE 4

(2-Chloro-4-thiophen-3-yl-phenyl)-(5H-10,11-dihydro-pyrrolo[2,1-c[]1,4] benzodiazepin-10-yl)-methanone Thiophene-3-boronic acid (0.51 g, 4 mmol) was added to a mixture of (4-bromo-2-chloro-phenyl)-(5H,11H-pyrrolo [2,1-c][1,4] benzodiazepin-10-yl-methanone of Example 1, Step A (1.61 g, 4 mmol) and sodium carbonate (1.02 g, 9.6 mmol) in toluene (36 mL), ethanol (10 mL) and water (20 mL). The resultant solution was purged with nitrogen for 10 minutes, then tetrakis (triphenylphosphine)palladium(0) catalyst (0.18 g, 0.16 mmol) was added. The reaction mixture was heated to reflux for 64 hours, cooled to ambient temperature, filtered through Celite, which was then rinsed with ethyl acetate. The combined filtrate was diluted to 140 mL with water-ethyl acetate (1:1), and the aqueous layer extracted with ethyl acetate. The combined extracts were dried over anhydrous magnesium sulfate, filtered and evaporated to dryness to yield a brown foam. Flash chromatography of the residue on silica gel Merck-60 (eluant: hexane-ethyl acetate 4:1) provided the title compound as a white solid, m.p.dec. 101° C.

$^1$H NMR (DMSO-$d_6$, 400 MHz): δ5.28 (br m, 4H), 5.90 (t, 1H), 5.99 (s, 1H), 6.81 (s, 1H), 7.03 (m, 3H), 7.37 (m, 2H), 7.55 (m, 3H), 7.74 (s, 1H), 7.99 (s, 1H)

MS (EI, m/z): 404 [M]$^+$

Anal. Calcd. for $C_{23}H_{17}ClN_2OS$: C, 68.23; H, 4.23; N, 6.92. Found: C, 67.98; H, 4.49; N, 6.88

EXAMPLE 5

[2-Chloro-4-(5-chloro-thiophen-3-yl-phenyl)-(5H-10,11-dihydro-pyrrolo[2,1-c][1,4] benzodiazepin-10-yl)-methanone 5-Bromo-2-chloro-thiophene (1.16 g, 5.79 mmol) was added to a mixture of 3-chloro-4-carboxyboronic acid (1.09 g, 5.5 mmol), triethylamine (4 mL) and tetrakis (triphenylphosphine)palladium(0) catalyst (0.2 g, 0.17 mmol) in pre-purged N,N-dimethylformamide (1 mL). The reaction mixture was heated to reflux for 24 hours, the solvent was concentrated in vacuo and the residue was taken into water. The aqueous solution was washed with ether and added to ice/concentrated hydrochloric acid (10 mL). The white precipitate was extracted into dichloromethane and the solution washed with brine. The combined extracts were dried over anhydrous magnesium sulfate, filtered, and evaporated to dryness to yield the expected acid (0.65 g).

The freshly prepared acid (0.65 g, 2.38 mmol) was dissolved in anhydrous tetrahydrofuran (20 mL). Oxalyl chloride (0.22 mL, 2.5 mmol) and N,N-dimethylformamide (1 drop) were added and the mixture was warmed to 35° C. for 10 minutes. The resultant solution was cooled to ambient temperature before being evaporated to dryness to give the crude acid chloride, which was used without further purification.

To a mixture of 10,11-dihydro-5H-pyrrolo[2,1-c][1,4]-benzodiazepine (0.417 g, 2.3 mmol) and diisopropylethylamine (0.5 mL, 2.8 mmol) in dichloromethane (10 mL) was added a solution of the crude acid chloride in dichloromethane (2 mL). The reaction was stirred at room temperature overnight. The organic solution was washed with 1N hydrochloric acid and brine, dried over anhydrous sodium sulfate, filtered and evaporated to dryness. Purification by flash chromatography on silica gel Merck-60 (eluant: hexane-ethyl acetate 2:1) provided the title compound (0.1 g) as a white solid, m.p. 97–99° C.

$^1$H NMR (DMSO-$d_6$, 400 MHz): δ5.00–5.35 (m, 4H), 5.91 (s, 1H), 5.99 (s, 1H), 6.81 (s, 1H), 7.1 (m, 3H), 7.21–8.01 (m, 6H) MS (EI, m/z): 438, 440, 442 [M]$^+$

EXAMPLE 6

(2-Methyl-4-thiophen-2-yl-phenyl)-(5,11-dihydro-pyrido[2,3-b][1,5] benzodiazepin-10-yl)-methanone Step A (4-Bromo-2-methyl-phenyl)-(5,11-dihydro-pyrido[2,3-b][1,5] benzodiazepin-6-yl)-methanone A suspension of 4bromo-2-methylbenzoic acid (4.9 g, 22.8 mmol) in dichloromethane containing a few drops of N,N-dimethylformamde was treated dropwise under nitrogen with oxalyl chloride (2.4 mL, 27.5 mol). After gas evolution subsided, the reaction mixture was refluxed for an additional 15 minutes and then evaporated to dryness in vacuo to provide the crude 4-bromo-2-methylbenzoyl chloride.

To a solution of 6,11-dihydro-5H-pyrido[2,3-b][1,5] benzodiazepine (3 g, 15.2 mmol) in N,N-dimethylformamide under nitrogen was added solid potassium carbonate (6.3 g, 45.6 mmol). A solution of the crude 4-bromo-2-methylbenzoyl chloride (22.8 mmol) in N,N-diethylformamide was added dropwise, and the mixture stirred at room temperature for 15 minutes. Excess potassium carbonate was filtered off, the filtrate was washed with water and the aqueous layer was extracted with chloroform. The extracts were dried over anhydrous sodium sulfate, evaporated to dryness and the residue dissolved in dichloromethane and absorbed onto a silica Merck-60 flash column. Elution with 20% ethyl acetate in hexane provided the title compound (3.2 g) as a foam which crystallized upon sonication from ethanol hexane.

$^1$H NMR (DMSO-$d_6$, 400 MHz): δ2.04 (s, 3H), 4.10 and 5.46 (dd, 2H), 6.54 (m, 1H), 6.68 (m, 1H), 6.78 (m, 1H), 6.90 (m, 1H), 7.00 (m, 1H), 7.18–7.29 (m, 1H), 8.10 (m, 1H), 9.55 (s, 1H)

MS (EI, rm/z): 393/395 [M]$^+$

Anal. Calcd. for $C_{20}H_{16}BrN_3O+0.05$ $C_2H_6O$: C, 60.89; H, 4.13; N, 10.61. Found: C, 60.49, H 4.07, N 10.44

Step B (2-Methyl-4-thiophen-2yl-phenyl)-(5,11-dihydro-pyrido[2,3-b][1,5] benzodiazepin-10-yl)-methanone To a solution of (4-bromo-2-methyl-phenyl)-(5,11-dihydro-pyrido [2,3-b][1,5] benzodiazepin-6-yl)-methanone (0.5 g, 1.27 mmol) of Step A, thiophene-2-boronic acid (0.167 g, 1.30 mmol) and sodium carbonate (0.595 g, 5.6 mmol) in toluene (20 mL), ethanol (10 mL) and water (10 mL) under nitrogen was added tetrakis (triphenylphosphine) palladium(0) catalyst (0.066 g, 0.057 mmol). The mixture was heated at reflux for 19 hours. Additional boronic acid (0.170 g, 1.30 mmol) and catalyst (0.050 g, 0.043 mmol) were added and reflux resumed for 3 hours. After stirring overnight at room temperature, the mixture was filtered through Celite and the cake washed with ethyl acetate. The combined organic layers were washed with water, dried over anhydrous sodium sulfate, and evaporated to dryness. The residue was dissolved in dichloromethane, absorbed onto a silica Merck-60 flash column and eluted with an ethyl acetate-hexane gradient (from 30 to 50%) to provide the title compound (0.29 g) as a foam, which crystallized as a white solid by trituration with diethyl ether/hexane, m.p. 118–120° C.

$^1$H NMR (DMSO-$d_6$, 400 MHz):δ2.11 (s, 3H), 4.10 and 5.49 (dd, 2H), 6.52 (m, 1H), 6.70 (m, 1H), 6.90–7.00 (m, 2H), 7.08 (m, 1H), 7.21–7.30 (m, 2H), 7.35 (m, 1H), 7.45 (m, 1H), 7.51 (m, 1H), 7.59 (m, 1H), 8.11 (m, 1H), 9.56 (s, 1H)

MS (EI, m/z): 397 [M]$^+$

Anal. Calcd. for $C_{24}H_{19}N_3OS$: C, 72.52, H, 4.82, N 10.57, Found: C 72.79, H 5.18, N 10.52

EXAMPLE 7

[2-Chloro-4-(5-chloro-thiphen-2-yl-phenyl]-(5,11-dihydro-pyrido [2,3-b][1,5] benzodiazepin-10-yl)-methanone Step A (4-Bromo-2-chloro-phenyl)-(5,11-dihydro-pyrido [2,3-b][1,5] benzodiazepin-10-yl)-methanone A suspension of 4-bromo-2-chlorobenzoic acid (5.4 g, 22.9 mmol) in dichloromethane (40 mL) containing a few drops of N,N-diethylformamide was treated dropwise under nitrogen with oxalyl chloride (2.4 mL, 27.5 mmol). After the gas evolution subsided, the reaction mixture was refluxed for an additional 15 minutes and evaporated to dryness in vacuo to provide the crude acid chloride.

To a solution of 6,11-dihydro-5H-pyrido[2,3-b][1,5] benzodiazepine (3 g, 15.2 mmol) in N,N-dimethylformamide under nitrogen were added solid potassium carbonate (6.3 g, 45.6 mmol). The mixture was treated dropwise with a solution of the crude 4-bromo-2-chlorobenzoyl chloride (22.9 mmol) in N,N-dimethylformamide. After stirring at room temperature for 15 minutes, water was added under stirring. The resulting solid was collected, dissolved in chloroform, and the solution washed with 1N NaOH and brine. The organic layer was dried over anhydrous sodium sulfate and evaporated to dryness. The residue (purple foam) was dissolved in dichloromethane and absorbed onto a silica Merck-60 flash column. Elution with 20% ethyl acetate in hexane provided 3.4 g of the title compound as a foam which crystallized as a white solid by trituration from ethanol-ether, m.p. 165–168° C.

$^1$H NMR (DMSO-d6, 400 MHz):δ4.13 and 5.42 (dd, 2H), 6.54 (m, 1H), 6.73–6.79 (m, 2H), 7.01 (m, 1H), 7.22–7.34 (m, 2H), 7.45 (m, 1H), 7.48–7.62 (m, 2H), 8.10 (m, 1H), 9.55 (s, 1H)

MS (EI, m/z): 413/415/417 [M]$^+$

Anal. Calcd. for $C_{19}H_{13}BrClN_3O$: C 55.03, H, 3.16, N 10.13, Found: C 54.81, H 3.15, N 9.86

Step B

[2-Chloro-4-(5-chloro-thiphen-2-yl)-phenyl]-(5,11-dihydro-pyrido[2,3-b][1,5] benzodiazepin-10-yl)-methanone 0.28 solvate with hexane To a solution of the (4-bromo-2-chloro-phenyl)-(5,11-dihydro-pyrido[2,3-b][1,5] benzodiazepin-10-yl)-methanone of Step A (0.5 g, 1.2 mmol), 5-chlorothiophene-2-boronic acid (0.21 g, 1.29 mmol) and sodium carbonate (0.57 g, 5.38 mmol) in toluene (20 mL), ethanol (10 mL) and water (10 mL) under nitrogen was added tetrakis(triphenylphosphine) palladium(0) catalyst (0.06 g, 0.052 mmol). The mixture was heated at reflux for 18 hours. Additional boronic acid (0.2 g, 1.29 mmol) and catalyst (0.065 g, 0.056 mmol) were added. After 5 hours the mixture was cooled and filtered through Celite which was then rinsed with ethyl acetate. The organic layer was washed with water, dried over anhydrous sodium sulfate, and evaporated to dryness. The residue was dissolved in dichloromethane and absorbed onto a column of flash silica gel Merck-60. Elution with 25% ethyl acetate in hexane provided the title compound (0.25 g) as a foam which crystallized as a pale yellow solid by trituration from ethanol-hexane, m.p. 131–134° C.

$^1$H NMR (DMSO-d$_6$, 400 MHz): δ4.14 and 5.44 (dd, 2H), 6.52 (m, 1H), 6.72–6.79 (m, 2H), 7.00 (m, 1H), 7.15 (m, 1H), 7.22–7.26 (m, 2H), 7.41–7.48 (m, 2H), 7.53–7.63 (m, 2H), 8.11 (m, 1H). 9.56 (s, 1H)

MS (EI, m/z): 451/453/455 [M]$^+$

Anal. Calcd. for $C_{23}H_{15}Cl_2N_3OS+0.28\ C_6H_{14}$: C 62.21, H 4.00, N 8.82, Found: C 62.07, H 3.98, N 8.96.

EXAMPLE 8

(2-Chloro-4-thiophen-3-yl-phenyl)-(5,11-dihydro-pyrido[2,3-b][1,5] benzodiazepin-10-yl)-methanone To a solution of the (4-bromo-2-chloro-phenyl)-(5,11-dihydro-pyrido[2,3-b][1,5] benzodiazepin-10-yl)-methanone of Example 7, Step A (0.5 g, 1.23 mmol), thiophene-3-boronic acid (0.158 g, 1.23 mmol) and sodium carbonate (0.568 g, 5.36 mmol) in toluene (20 mL), ethanol (10 mL) and water (10 mL) under nitrogen was added the tetrakis (triphenylphosphine) palladium(0) catalyst (0.06 g, 0.052 mmol). The reaction was heated at reflux for 20 hours, cooled, and filtered through Celite, which was then rinsed with ethyl acetate. The organic layer was washed with water, dried over sodium sulfate and evaporated to dryness. The residue (blue-green oil) was dissolved in dichloromethane and absorbed onto a silica Merck-60 flash column. Elution with 25% ethyl acetate in hexane yielded a foam (0.24 g) which was triturated with diethyl ether-hexane to provide the title compound as a white solid, m.p. 125–130° C.

$^1$H NMR (DMSO-d$_6$,400 MHz): 4.14 and 5.45 (dd, 2H), 6.51 (m, 1H), 6.76–6.80 (m, 2H), 6.99 (m, 1H), 7.22–7.26 (m, 2H), 7.54–7.71 (m, 5H), 7.98 (m, 1H), 8,11 (m, 1H), 9.56 (s, 1H)

MS (EI, m/z): 417/419 [M]$^+$

Anal. Calcd. for $C_{23}H_{16}ClN_3OS$: C 66.10, H 3.86, N 10.05, Found: C 66.38, H 4.11, N 9.85

What is claimed:

1. A compound which is selected from the group of

[4-(5-bromo-thiophen-2-yl-phenyl]-(5H-10,11-dihydro-pyrrolo[2,1-c][1,4] benzodiazepin-10-yl)-methanone;

[2-chloro-4-(5-chloro-thiophen-3-yl)-phenyl]-(5H-10,11-dihydro-pyrrolo[2,1-c][1,4] benzodiazepin-10-yl)-methanone;

(2-chloro4-thiophen-2-yl-phenyl)-(5H-10,11-dihydro-pyrrolo[2,1-c][1,4] benzodiazepin-10-yl)-methanone;

[2-chloro-4-(5-chloro-thiophen-2-yl)-phenyl]-(5H-10,11-dihydro-pyrrolo[2,1-c][1,4] benzodiazepin-10-yl)-methanone;

[2-chloro-4-(5-methyl-thiophen-2-yl)-phenyl]-(5H-10,11-dihydro-pyrrolo[2,1-c][1,4] benzodiazepin-10-yl)-methanone;

(2-chloro-4-thiophen-3-yl-phenyl)-(5H-10,11-dihydro-pyrrolo[2,1-c][1,4] benzodiazepin-10yl)-methanone;

[2-chloro-4-(5-chloro-thiophen-3-yl)phenyl]-(5H-10,11-dihydro-pyrrolo[2,1-c][1,4] benzodiazepin-10-yl)-methanone;

(2-methyl-4-thiophen-2-yl-phenyl)-(5,11-dihydro-pyrido[2,3-b][1,5] benzodiazepin-10yl)-methanone;

[2-chloro-4-(5-chloro-thiophen-2-yl)-phenyl]-(5,11-dihydro-pyrido [2,3-b][1,5] benzodiazepin-10-yl)-methanone; or (2-chloro4-thiophen-3-yl-phenyl)-(5,11-dihydro-pyrido[2,3-b][1,5] benzodiazepin-10-yl)-methanone;

or a pharmaceutically acceptable salt thereof.

2. A method of treating urinary disorders in a mammal selected from the group of diabetes insipidus, nocturnal enuresis, nocturia or urinary incontinence, the method comprising administering to the mammal in need thereof a pharmaceutically effective amount of a compound of the formula:

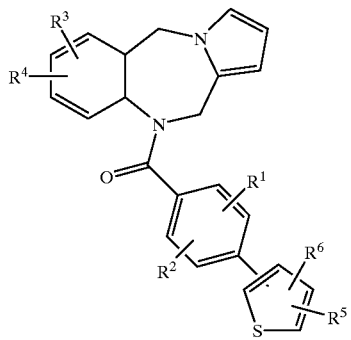

wherein:
R[1], R[2], R[5] and R[6] are independently, selected from hydrogen, lower alkyl ($C_1$–$C_6$), lower alkoxy ($C_1$–$C_6$), halogen, and $CF_3$;

R[3], and R[4] are independently, selected from the group comprising hydrogen, lower alkyl ($C_1$–$C_6$), halogen, amino, ($C_1$–$C_6$) lower alkoxy, or ($C_1$–$C_6$) lower alkylamino;

or a pharmaceutically accepted salt form thereof.

3. A method according to claim 2 in which the compound is (4-thiophen-2-yl-phenyl)-(5H-10,11-dihydro-pyrrolo[2,1-c][1,4] benzodiazepin-10-yl)-methanone or a pharmaceutically acceptable salt thereof.

4. A method according to claim 2 in which the compound is [4-(5-bromo-thiophen-2-yl-phenyl]-(5H-10,11-dihydro-pyrrolo[2,1-c][1,4] benzodiazepin-10-yl)-methanone.

5. A method according to claim 2 in which the compound is [2-chloro-4-(5-chloro-thiophen-3-yl)-phenyl]-(5H-10,11-dihydro-pyrrolo[2,1-c][1,4] benzodiazepin-10-yl)-methanone.

6. A method according to claim 2 in which the compound is (2-chloro-4-thiophen-2-yl-phenyl)-(5H-10,11-dihydro-pyrrolo[2,1-c][1,4] benzodiazepin-10-yl)-methanone.

7. A method according to claim 2 in which the compound is [2-chloro-4-(5-chloro-thiophen-2-yl)-phenyl]-(5H-10,11-dihydro-pyrrolo[2,1-c][1,4] benzodiazepin-10-yl)-methanone.

8. A method according to claim 2 in which the compound is [2-chloro-4-(5-methyl-thiophen-2-yl)-phenyl]-(5H-10,11-dihydro-pyrrolo[2,1-c][1,4] benzodiazepin-10-yl)-methanone.

9. A method according to claim 2 in which the compound is (2-chloro-4-thiophen-3-yl-phenyl)-(5H-10,11-dihydro-pyrrolo[2,1-c][1,4] benzodiazepin-10-yl)-methanone.

10. A method according to claim 2 in which the compound is [2-chloro-4-(5-chlorothiophen-3-yl)-phenyl]-(5H-10,11-dihydro-pyrrolo[2,1-c][1,4] benzodiazepin-10-yl)-methanone.

11. A method of promoting temporary delay of urination in a mammal, the method comprising administering to the mammal in need thereof a pharmaceutically effective amount of a compound of the formula:

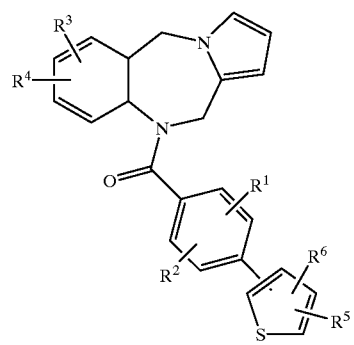

wherein:
R[1], R[2], R[5] and R[6] are independently, selected from hydrogen, lower alkyl ($C_1$–$C_6$), lower alkoxy ($C_1$–$C_6$), halogen, and $CF_3$;

R[3], and R[4] are independently, selected from the group comprising hydrogen, lower alkyl ($C_1$–$C_6$), halogen, amino, ($C_1$–$C_6$) lower alkoxy, or ($C_1$–$C_6$) lower alkylamino;

or a pharmaceutically accepted salt form thereof.

* * * * *